United States Patent [19]

Barthelmes et al.

[11] Patent Number: 4,587,471
[45] Date of Patent: May 6, 1986

[54] HANDLE ASSEMBLY FOR AN X-RAY EXAMINATION APPARATUS

[75] Inventors: Norbert Barthelmes, Erlangen; Werner Woelfel, Hessdorf, both of Fed. Rep. of Germany

[73] Assignee: Siemens Aktiengesellschaft, Berlin & Munich, Fed. Rep. of Germany

[21] Appl. No.: 513,015

[22] Filed: Jul. 12, 1983

[30] Foreign Application Priority Data

Sep. 29, 1982 [DE] Fed. Rep. of Germany ....... 3236116

[51] Int. Cl.⁴ .............................................. G05B 11/01
[52] U.S. Cl. ....................................... 318/628; 318/2; 318/488
[58] Field of Search ............... 318/628, 488, 2; 338/2, 338/5

[56] References Cited

U.S. PATENT DOCUMENTS

| | | | |
|---|---|---|---|
| 3,075,160 | 1/1963 | Starr | 338/2 X |
| 3,836,834 | 9/1974 | Abbatiello et al. | 318/488 X |
| 3,866,048 | 2/1975 | Gieschen | 318/628 X |
| 3,986,090 | 10/1976 | Hecker et al. | 318/488 |
| 4,021,715 | 5/1977 | Von Hacht | 318/628 |
| 4,107,590 | 8/1978 | Pury et al. | 318/628 |

FOREIGN PATENT DOCUMENTS 2739934 3/1979 Fed. Rep. of Germany .

Primary Examiner—B. Dobeck
Attorney, Agent, or Firm—Hill, Van Santen, Steadman & Simpson

[57] ABSTRACT

A handle assembly for an x-ray examination apparatus for permitting a technician to position the apparatus above a patient with the aid of a support motor has a grip connected to the apparatus by two support elements, each of the support elements having a defined weak point, such as a segment of reduced thickness, and a plurality of control elements for operating the support motor in response to stresses experienced by the weak point caused by pulling on the grip. The control elements are connected between the support elements and the apparatus, spanning each weak point. Two control elements, disposed at right angles to each other, may be utilized for each weak point.

9 Claims, 2 Drawing Figures

HANDLE ASSEMBLY FOR AN X-RAY EXAMINATION APPARATUS

BACKGROUND OF THE INVENTION

1. Field of the Invention

The present invention relates to a handle assembly for an X-ray examination apparatus, and in particular to such a handle assembly for permitting a technician to adjust the three-dimensional position of the apparatus with the aid of a support motor.

2. Description of the Prior Art

Many types of X-ray examination installations have apparatus components, such as spot film devices, which must be adjusted precisely with respect to a patient to be examined but which are too heavy to be adjusted soley by hand, thus requiring the aid of a support motor to effect such adjustment. Conventional support motors utilize for this purpose generally have a slip friction clutch, the output torque of which is carefully adjusted so as to be just below that torque necessary to adjust the apparatus against the force of gravity. The torque of the slip friction clutch is utilized in combination with the force supplied by a technician by hand to overcome gravitational and inertial forces opposing movement of the apparatus. Such support motors are customarily connected through a suitable hand switch housed in the handle assembly. The sudden connection of the torque of the support motor to the apparatus, after overcoming the restoring force of the manual switch, causes an undesired jerky starting motion of the apparatus component, particularly in the case of X-ray examination installations.

A handle assembly is disclosed in German OS No. 2739934 for displacing an apparatus component with the aid of a support motor wherein the grip portion of the handle assembly is in the form of a sleeve which is displaceably mounted in the longitudinal direction on the handle assembly. The ends of the sleeve respectively abut discs comprised of pressure-sensitive resistance material. The resistance material is interconnected in a branch of a bridge circuit associated with the control circuitry for the support motor. This handle assembly permits the apparatus component to be displaced in a relatively jerk-free manner. Additionally, substantially no switching play is felt on the handle assembly. This assembly has the disadvantage, however, of permitting control of the component in only one positioning or adjusting dimension. Moreover, construction of such a handle assembly is relatively costly and, because of the close tolerances which must be observed for the individual components, is not simple to properly adjust.

SUMMARY OF THE INVENTION

It is an object of the present invention to provide a handle assembly for moving a heavy component with the aid of a support motor which permits two-dimensional jerk-free adjustment of the component.

It is a further object of the present invention to provide such a handle assembly which can be actuated in a manner substantially free from play.

Another object of the present invention is to provide such a handle assembly having relatively few structural components which is relatively simple to adjust properly.

The above objects are inventively achieved in an X-ray examination apparatus wherein the handle assembly has a grip connected to the apparatus by support elements, each of the support elements having a defined weak point which exhibits a slight deformation as a technician applies force by hand to the grip. A plurality of control elements are connected at one side to the apparatus and at their respective other sides to the support members, so as to span the weak point of the support member. The control elements are responsive to deformation of the weak point, and are interconnected in the control circuitry for the support motor. A unitary handle assembly is thus achieved which permits adjustment of the apparatus component by means of the support motor, with substantially no switching play. Moreover, adjustment of the control elements, because of the defined rest or standby position of the handle, is relatively simple.

Additionally, the structure disclosed herein is easily adaptable for two-dimensional control of the drive means for the apparatus. In a two-dimensional embodiment of the invention, at least two control elements are utilized which abut the handle assembly at right angles relative to each other, and a support motor is associated with each of the control elements for respectively adjusting the apparatus in two dimensions.

A particularly stable mounting of the grip of the handle assembly is achieved in an embodiment of the invention wherein the grip is connected at its opposite ends to a supporting member, each of the supporting members having a weak point defined by a reduced thickness and/or width. This structure has the advantages that all torques which may potentially falsify the signals of the control elements, which would otherwise arise due to eccentric or off-grasping of the grip, cancel each other.

DESCRIPTION OF THE PREFERRED EMBODIMENTS

Figure 1:
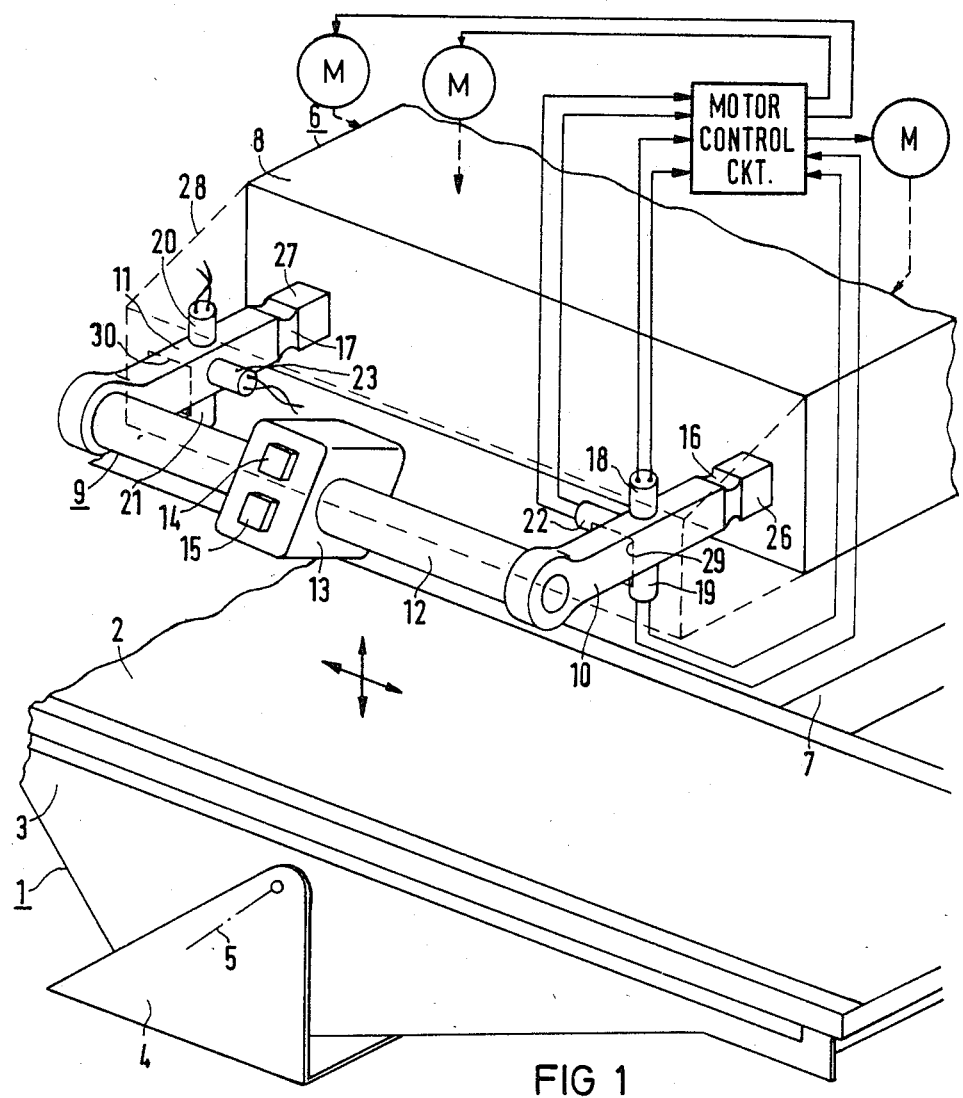
FIG. 1 is a perspective view of a handle assembly for an X-ray examination apparatus constructed in accordance with the principles of the present invention disposed above a patient support platform.

An X-ray examination apparatus generally referenced at 1 is shown in FIG. 1 which employs a handle assembly constructed in accordance with the principles of the present invention. The apparatus 1 includes a patient support platform 2 mounted on a table frame 3. The frame 3 is tiltable on a stand 4 about a horizontal axis 5. A component 6 of the X-ray examination apparatus, such as a spot film device, is disposed above the patient platform 2 and is aligned substantially parallel therewith. The component 6 is mounted and supported on a longitudinally extending carriage 7 which is displaceable on the frame 3 in the longitudinal direction of the patient support platform 2. The component 6 is also displaceable transversely and perpendicularly to the patient support platform 2 in a manner known to those skilled in the art not illustrated in greater detail in FIG. 1. The component 6 has a housing 8 to which a handle assembly 9 is welded. The handle assembly 9 consists of two support mounting members 10 and 11, between which a grip 12 extends. The handle assembly 9 has a control box 13 centrally mounted on the grip 12 which carries two control push buttons 14 and 15.

As shown in FIG. 1, the support mounting members 10 and 11 respectively exhibit a defined weak point 16 and 17 in the form of a segment of reduced width and-/or thickness. The support member 10 carries pressure-dependent resistance elements 18, 19 and 22. The support member 11 carries identical pressure-dependent resistance elements 20, 21 and 23.

Figure 2:
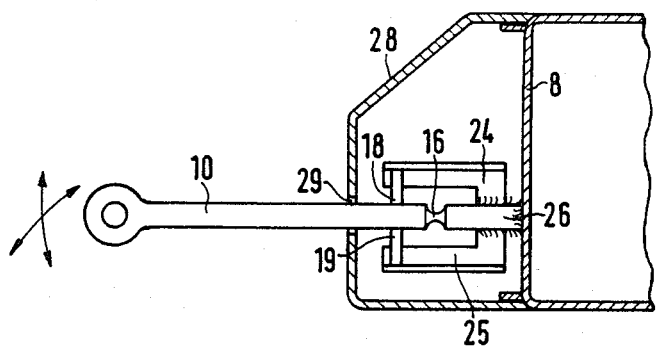
FIG. 2 is a side view, partly in section, of the structure for mounting the handle assembly shown in FIG. 1 to the apparatus component.

As shown in FIG. 2 (omitted in FIG. 1 for clarity) the pressure-dependent resistance elements 18 and 19 are connected to that portion of the support member 10 on the side of the weak point 16 away from the component 6. The support element 10 is directly welded to the housing 8 of the component 6. In this embodiment, the weak point 16 is in the form of a rounded notch extending annularly around the support member 10. Elbow connectors 24 and 25 (only two of which can be seen in FIG. 2) are welded to a segment 26 of the support element 10 disposed between the weak point 16 and the housing 8. Each resistance element and the connector attached thereto form a control assembly. An identical arrangement is utilized to connect the pressure-dependent resistance elements for the support member 11 to a segment 27 thereof. A hood 28 having rectangular openings 29 and 30 therein for respectively receiving the support members 10 and 11 is attached to the housing 8.

The pressure-sensitive resistant components 18 through 23 are connected through a motor control circuit to support motor M respectively connected to the component 6 by suitable drive trains (schematically shown by dashed lines) for displacing the component 6 perpendicularly to the plane of the table 2. One such connection is schematically represented for the element 18, the support motor being referenced at M.

If a technician wishes to manually upwardly push the component 6 in order, for example, to permit a patient to rise from the patient support platform 2, as the grip 12 of the handle assembly 9 is pushed upward, the assembly 9 bends at approximately the region of the two weak points 16 and 17. The two pressure-dependent resistance elements 18 and 20, shown in FIG. 1 abutting the upper side of the support members 10 and 11, are thus compressed. These pressure-sensitive resistant elements are connected to the control circuitry for the support motor which effects vertical displacement of the component 6, and control the output torque thereof in a known manner as described, for example, in German OS No. 2739934 corresponding to the amount of compression of those elements. Thus only a small force need be exerted by the technician in order to cause the support motor to take over control of the displacement of the component 6, so that the technician has the impression of raising a relatively lightweight component.

If the handle assembly 9 is displaced toward the left, that is, in the longitudinal direction of the grip 12, the pressure-dependent resistance element 22, abutting the interior side of the support element 10, is compressed. The element 22 is connected to the support motor which effects displacement of the component 6 in a longitudinal direction relative to the table 2 in accordance with the magnitude of the applied manual force. It should be noted that the terms "longitudinal" and "vertical" are utilized in accordance with the placement of the table 2 as shown in FIG. 1. If the table 2 is itself vertically placed in a position perpendicular to that shown in FIG. 1, it can be accomodated with the same handle assembly 9, however, "longitudinal" displacement for the arrangement shown in FIG. 1 then becomes "vertical" displacement. The technician still has the impression of adjusting a lightweight component 6.

It will be apparent to those skilled in the art that other types of transducers such as, for example, piezo-elements may be utilized in place of pressure-dependent resistance elements. In such an embodiment, however, an amplifier must be associated with each piezo-element, the outputs of the amplifiers being utilized to trigger triacs connected in the motor current circuit.

Although other modifications and changes may be suggested by those skilled in the art it is the intention of the inventors to embody within the patent warranted hereon all changes and modifications as reasonably and properly come within the scope of their contribution to the art.

We claim as our invention:

1. A handle assembly for moving a heavy component with the aid of a motive means drivingly connected to said component and having control circuitry for controlling the operation of said motive means, said handle assembly comprising:
   a support means rigidly connecting said assembly to said component, said support means having at least one defined mechanically weak point; and
   a plurality of control assemblies electrically connected to said control circuitry and mechanically connected between said support means and said component spanning said weak point, said control assemblies each generating an electric signal for use by said control circuitry for operating said motive means for moving said component in response to deformation exhibited by said weak point upon the application of force to said handle assembly.

2. A handle assembly as claimed in claim 1 wherein the number of control assemblies is at least two and wherein said control assemblies are connected to said handle assembly at right angles relative to each other, and wherein said motive means comprises a like plurality of support motors respectively connected to each of said control assemblies.

3. A handle assembly as claimed in claim 1 wherein said handle assembly further comprises a grip having opposite free ends, and wherein said support means comprises a pair of support members respectively connected to said free ends of said grip, each of said support members having a defined mechanically weak point.

4. A handle assembly as claimed in claim 2 wherein said motive means comprises a plurality of support motors and wherein at least one control assembly is connected to a support motor for vertically moving said component and at least one other control assembly is connected to a support motor for horizontally moving said component.

5. A handle assembly as claimed in claim 1 wherein said motive means includes respective means for moving said component along different axes and wherein said plurality of control assemblies includes different control elements for responding to deformation along each of said axes caused by said weak point, said control elements being respectively connected to one of said respective motive means for effecting movement of said component along the same axis associated with said control element.

6. A handle assembly as claimed in claim 1 wherein each of said control assemblies includes a pressure-dependent resistance element mounted on said support means and a rigid connector extending across said weak point and mechanically connecting said resistance element and said support means.

7. A handle assembly as claimed in claim 1 wherein said control assemblies each include a piezo-element mounted on said support means and a rigid connector extending across said weak point and mechanically connecting said piezo-element and said support means.

8. A handle assembly as claimed in claim 1 wherein said component is a component of an X-ray examination apparatus disposed above a patient support platform.

9. A handle assembly as claimed in claim 1 wherein said motive means includes a support motor for adjusting said component perpendicularly to the plane of said patient support platform and at least one control assembly connected to said support motor for supplying a signal to said control circuitry for adjusting the position of said component along the length of said patient support platform.

* * * * *